US006896011B2

(12) United States Patent
Talamona (10) Patent No.: US 6,896,011 B2
(45) Date of Patent: May 24, 2005

(54) DEVICE AND PROCESS FOR FILLING A COLUMN WITH A FILLER MATERIAL

(75) Inventor: Angelo Talamona, Flawil (CH)

(73) Assignee: Büchi Labortechnik AG, Flawil (CH)

(*) Notice: Subject to any disclaimer, the term of this patent is extended or adjusted under 35 U.S.C. 154(b) by 135 days.

(21) Appl. No.: 10/350,060

(22) Filed: Jan. 24, 2003

(65) Prior Publication Data
US 2003/0183299 A1 Oct. 2, 2003

(30) Foreign Application Priority Data
Mar. 27, 2002 (EP) .............................. 02405241

(51) Int. Cl.[7] .............................................. B65B 1/04
(52) U.S. Cl. ................................ 141/8; 141/59; 141/65
(58) Field of Search ............................. 141/7, 8, 59, 65; 210/148.2

(56) References Cited

U.S. PATENT DOCUMENTS 4,175,037 A * 11/1979 Benney et al. ................ 141/12
5,249,610 A * 10/1993 Cassou et al. ............... 141/130
6,213,171 B1 * 4/2001 Saint-Ramon et al. ........ 141/59

FOREIGN PATENT DOCUMENTS

| EP | 0279257 | 1/1988 |
| JP | 59182317 | 10/1984 |
| WO | WO95/29009 | 11/1995 |

* cited by examiner

Primary Examiner—Gregory L. Huson
Assistant Examiner—Peter deVore
(74) Attorney, Agent, or Firm—Shoemaker and Mattare (57) ABSTRACT

A device and a process are used for filling a column with a filler material. The column is provided on two ends with a fill opening or with an intake opening. The column is held by a holding device. Using the holding device the column can be inserted in a tank in which the filler material is located. The column is connected via a connecting line to a negative pressure source. By producing a negative pressure in the interior of the column the filler material can be sucked homogeneously into the interior of the column.

16 Claims, 6 Drawing Sheets

DEVICE AND PROCESS FOR FILLING A COLUMN WITH A FILLER MATERIAL

BACKGROUND OF THE INVENTION

The invention relates to a process and a device for filling a column with a filler material.

In chromatography so-called separation columns are used. The separation columns are provided with a separation material which is intended to retain selectively the substances contained in a sample. The separation material of the separation columns which are used for example in preparative chromatography are typically silica gels or modified silica gels.

The silica gel which is used typically has a size of a few dozen microns. In order to obtain qualitatively adequate analysis results, it is necessary for the separating medium, for example silica gel, to be homogeneously distributed over the entire length and the entire cross section of the separation column. Separation columns are at present delivered to the user completely packed with the separating medium; the user uses them in a chromatography device. This approach has the disadvantage that as a result of vibrations during transport, a nonuniform distribution of the separating medium in the separation column can occur. Silica gel has particles with different sizes which correspond to a certain size distribution. Vibrations can lead to separation of particles with different grain sizes, so that, for example, larger particles settle to the bottom due to vibrations. The problem of separation during transport can be solved by filling the column with the separating medium directly by the user. JP 08-094603 discloses for example a method with which separation columns for liquid chromatography can be packed. The column is filled by producing a vacuum on one end of the column. The powdered separating medium is sucked into the column by opening a valve. At the same time as intake, knocking occurs. One disadvantage in this arrangement is that nonhomogeneities can occur as a result of feed through a pipeline when the separation column is being filled with the separating material. Moreover the process suggested therein is comparatively complex, since the separation column must be provided on both sides with connections for filling and evacuation. Therefore efficient filling is not possible.

SUMMARY OF THE INVENTION

An object of this invention is to devise a device and a process for filling and refilling columns in which homogenous filling of the separation column is easily and efficiently possible.

These objects are achieved with a device and process described below.

The device is used to fill a column which has an opening on two ends. The term "column" is defined as an elongated container of any cross sectional shape. The column is to be filled with a filler material. In particular, the column will be used as a separation column for chromatography and will be filled with a separating medium. The device has a tank for holding the filler material. The device is moreover provided with a holding device, which is used to hold the column. Moreover the device has a connecting line which provides an airtight connection of the intake opening on one end of the column to a negative pressure source. The column can be inserted into the tank by means of the holding device, with one fill opening on the other end of the column. To suck the filler material out of the tank into the column, a negative pressure can be produced with the negative pressure source.

In many laboratories there are already negative pressure sources. Laboratory personnel are familiar with the operation of these devices. The negative pressure source is thus easily used to fill a separation column. The separating material can be easily kept in the tank, and, since the tank does not move, there is little or no danger of separation. Because the column can be inserted into the tank by means of the holding device, the column can be filled very quickly. Connection of the feed line for the filler medium to the fill opening of the column is not necessary for this purpose. Moreover, the immersion of the column into the filler material contained in the tank leads to the column being filled very quickly and linearly. This also ensures that no separation or nonhomogeneities arise during filling.

According to a first preferred embodiment, the tank is filled with means for fluidizing the filler material. Fluidizing of the filler material which consists of very small particles ensures that the filter material remains homogeneously distributed in the tank itself. For example, the fluidizing means can be formed by a compressed air source by which air can be blown into the tank, for example from the bottom. Compressed air is generally available in the laboratory. Therefore fluidizing can take place without major effort.

According to one preferred embodiment, the device has a fill station, a sealing station and preferably a cleaning station. The column can be moved between the stations preferably by swivelling the column along a circular path on which the stations are located.

According to another preferred embodiment, the cleaning station has means which are used for removing excess filler material in the area of the fill opening. The means for removing the excess filler material can for example have a rotary doctor blade having a width which corresponds roughly to the free inside diameter of a cylindrically shaped column. The height of the doctor blade corresponds roughly to the length of the section on the end of the column which is not to be filled. An unfilled section on the end of the column is desirable so that the column can be sealed.

The sealing station typically has means for inserting a sealing body into the fill opening of the column. The sealing body can consist for example of a frit of porous material, for example, of polyethylene, PTFE or glass.

According to another preferred embodiment, the holding device is made vertically adjustable. In this way the column can be immersed into the filler material in the tank by lowering the holding device. At the same time the filled column can be cleaned by lowering it onto the means for removing the excess material, for example onto the rotary doctor blade in the above described form. Finally, the vertically adjustable arrangement of the column also allows simple insertion of a sealing body, for example a frit, by lowering the column onto a bearing which carries one such sealing body. Typically the negative pressure source is designed to produce a negative pressure in the range from 10 mbar to 1 mbar, in any case less than 400 mbar. It has been shown that with this negative pressure, the filler material can be sucked rather quickly into the column and that as a result of the generated negative pressure, the filler material is also held in the separation column against gravity. This is especially advantageous when the column is moved by lowering in the vertical direction into the fill, cleaning or sealing station.

Advantageously the connecting line can have a valve arrangement for connecting the negative pressure source to the column. The connecting line can be closed with the valve arrangement. In this way it is easily possible to start up the negative pressure source first, then insert the column into the tank and only when the column is in the desired position, to produce the negative pressure in the column.

The holding device can moreover be provided with a stop which exactly defines the immersion depth of the column into the tank.

In practicing the invention, a column which is open on two ends is filled with a filler material. The column is used especially as a separation column for chromatography. Therefore typically the column is filled with a separating medium. In a first step the column is inserted into a tank in which the filler material is located. In the next step, a negative pressure is produced within the column. The negative pressure is used to suck the filler material through the fill opening on one end of the column into the column. As soon as the column is filled with filler material, it is removed from the tank.

According to one preferred embodiment, the column with the fill opening on its bottom end is lowered into the tank.

After filling and removing the column from the tank, the fill opening can be sealed. This can be accomplished by inserting a frit of porous material. The advantage of such a seal is that the frit does not adversely affect the separating process during chromatography. Before sealing the column, it can be cleaned, at least in the area of the fill opening on its inside, so that the frit can be easily inserted.

It is moreover conceivable and preferred that before filling the column or before connecting the column to the negative pressure source, an air-permeable sealing element, especially a frit of porous material, is attached to the intake opening of the column. This yields various advantages. On the one hand, the column is also sealed in this way at the intake opening. If the sealing element is attached before filling, the air-permeable sealing element acts to a certain extent as a retaining element which prevents the filler material from being sucked through the connecting line in the direction of the negative pressure source.

Preferably the filler material in the tank is fluidized before or even during the filling of the column. It is conceivable for the filler material to be fluidized by shaking or stirring; however, fluidizing by blowing air or other gases (for example, inert gases) into the tank is preferred.

The column can be inserted by the holding device into the tank. Here it is both conceivable for the column to be lowered with the holding device or alternatively to lift the tank. Other movements are also conceivable. For example, by swivelling it out of the horizontal position into the vertical position the column can be immersed into the filler material which is located in the tank.

Alternatively to movement between the individual stations along a circular path it is also conceivable to move the column linearly or even to arrange the column to be stationary and to move the cleaning station, sealing station and fill station, for example to push them. Different mechanical approaches to cleaning or sealing the fill opening of the column are also conceivable, without departing from the framework of the invention. Cleaning can also be done by wiping with a brush.

BRIEF DESCRIPTION OF THE DRAWINGS

Embodiments of the invention are described below with reference to the drawings, wherein.

DESCRIPTION OF THE PREFERRED EMBODIMENT(S)

Figure 1:
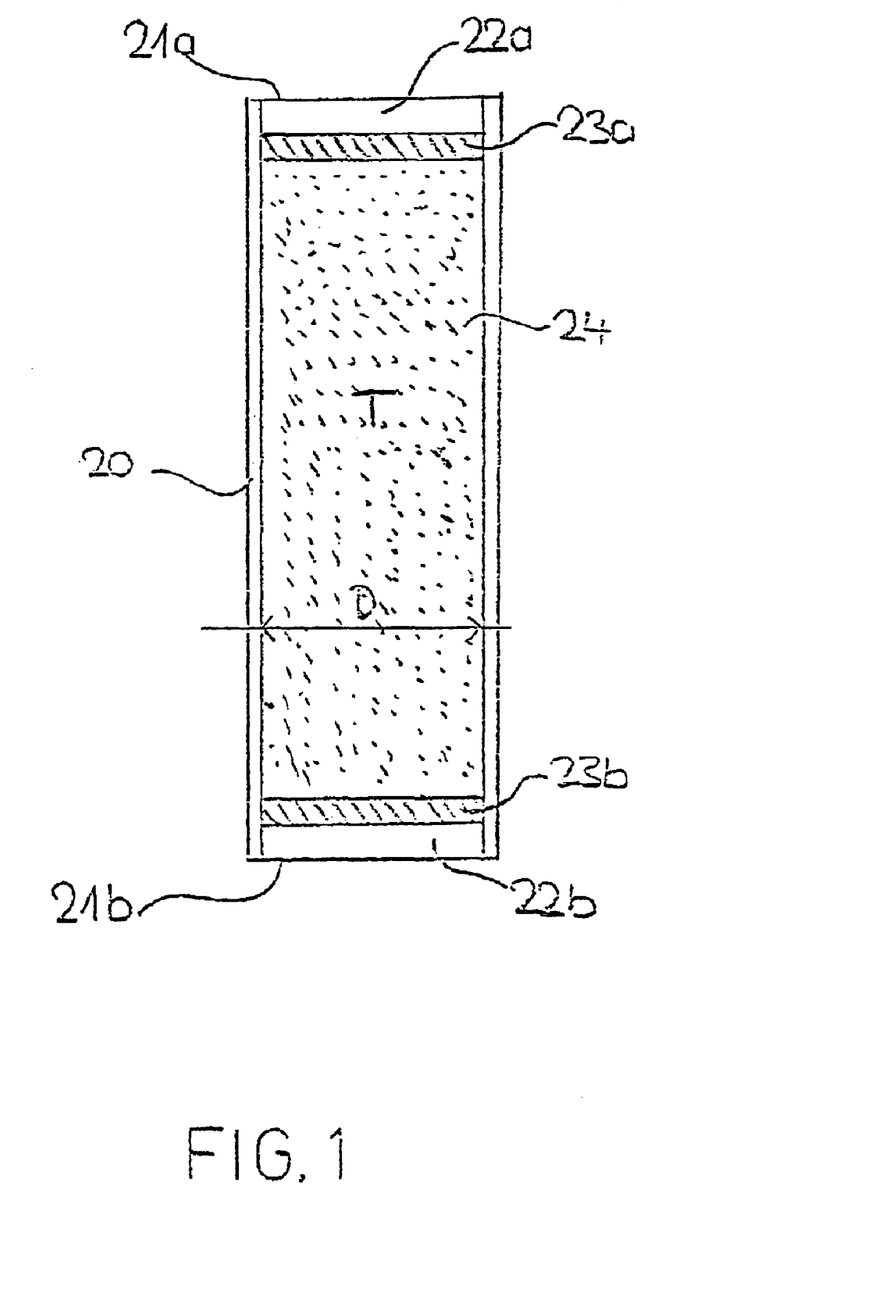
FIG. 1 is a schematic of a filled separation column as claimed in the invention.

FIG. 1 shows a separation column 20 which is filled with the separating medium T. The separation column 20 is a precision manufactured tube of polyethylene or of glass. The tube typically has a wall thickness of 1–2 mm (and any inside diameter D). The separation column 20 has an interior 24 which is homogeneously filled with the separating material T. The separation column 20 is provided on the top end 21a with a first opening 22a and on the bottom end 21b with a second opening 22b. The opening 22a on the top end 21a is sealed with a frit 23a. The frit 23a may be made of polyethylene and has a disk shape with a diameter which corresponds roughly to the free inside diameter D of the tube of the separation column 20 so that the fit is held non-positively in the tube. The opening 22b on the bottom end 21b of the separation column 20 is sealed with a flit 23b. The separation column 20 on its ends 21a, 21b has suitable connecting means (not shown) which allow insertion of the column into conventional chromatography devices. These connecting means, which are not shown in detail, can also be used to connect the separation column 20 to a connecting line 13 (see FIG. 2). Typically silica gel with an average grain size from 40 to 65 microns is used as the separating material T. These separating materials are used for example for preparative liquid chromatography.

Figure 2:
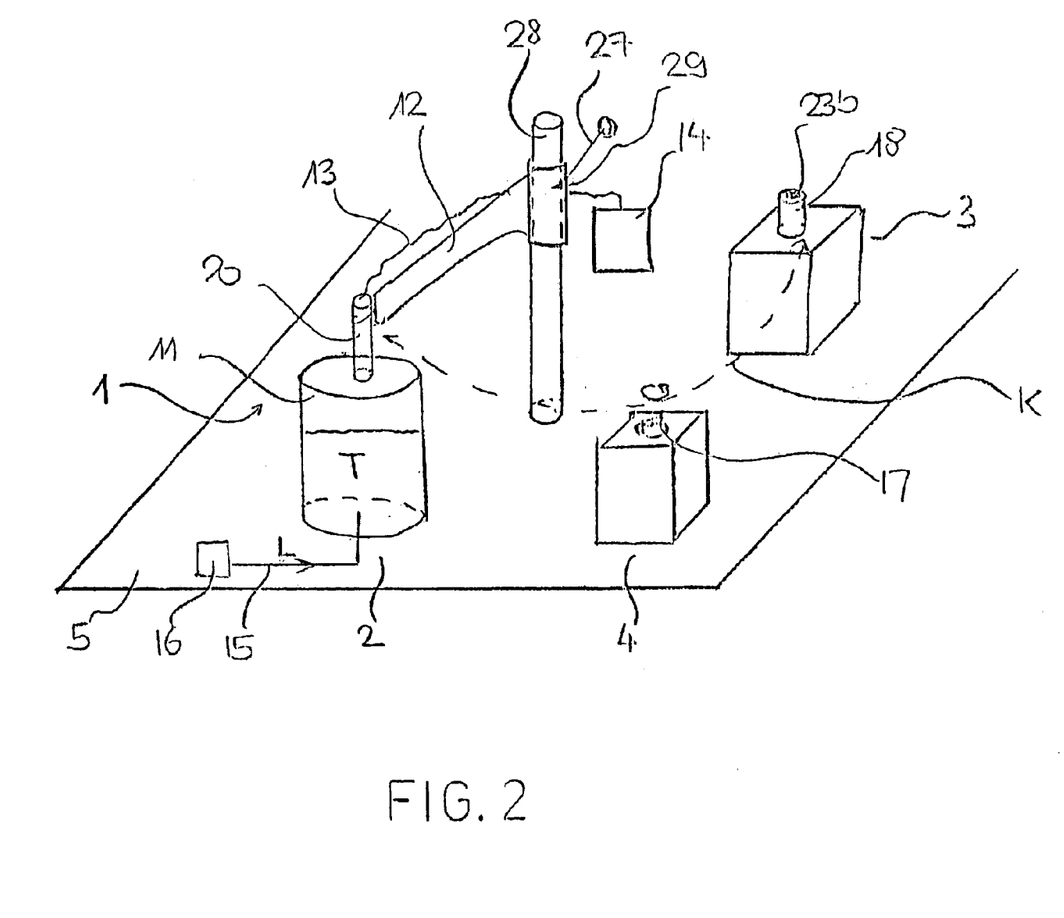
FIG. 2 is a schematic of the device as claimed in the invention in perspective form.

FIG. 2 schematically shows the device 1 which is used to fill the separation column 20 according to FIG. 1. The device 1 has a base plate 5 on which there are a fill station 2, a sealing station 3 and a cleaning station 4.

The fill station 2 comprises a tank 11. The tank is designed to hold an amount of filler material which is used to fill several columns. The column 20 is held by means of a holding device 12 which can move and swivel in the axial direction along a support rod 28. One arm 29 of the holding device 12 is attached to a sleeve which slides along the support rod 28. A lever 27 is used to fix the holding device 12 in the axial and in the swivelling direction. The tank 11 is provided with a compressed air fine 15 through which compressed air L can be blown into the tank 11 by means of a compressor 16. In this way, the separating medium T contained in the tank can be fluidized. The device moreover has a connecting line 13 by means of which the column 20 can be connected to a negative pressure source 14. To fill the column 20 with the separating medium T, the column is immersed by lowering the holding device 12 into the tank 11 (see also FIG. 3). As soon as the column 20 is immersed deeply enough in the tank 11, a vacuum is produced with the negative pressure source 14 within the column 20. In this way the separating medium T is intaken quickly and uniformly into the interior 24 of the column 20. As soon as the separation column 20 is filled, it is removed by lifting the holding device 12 out of the tank 11.

In the next step the separation column 20 is swivelled to the cleaning station 4 by swivelling the holding device 12 along the circular path K. The cleaning station 4 has a rotary doctor blade 17 by means of which excess separating material T can be scraped off on the bottom end 21b of the separation column.

As soon as the excess separating material has been removed, the separation column 20 is moved again by swivelling along the circular path K to the sealing station 3. The sealing station 3 has a storage space 18 on which a frit 23b for sealing the bottom end 21b of the column 20 is stored.

Before filling the column 20, the column or the device is prepared as follows: On the top end 21a a frit 23a is inserted into the intake opening 22a. Then the top end 21a or the intake opening 22a of the column 20 is connected by the coupling piece 25 (see FIG. 3) to the connecting line 13 and thus to the negative pressure source 14.

Figure 3:
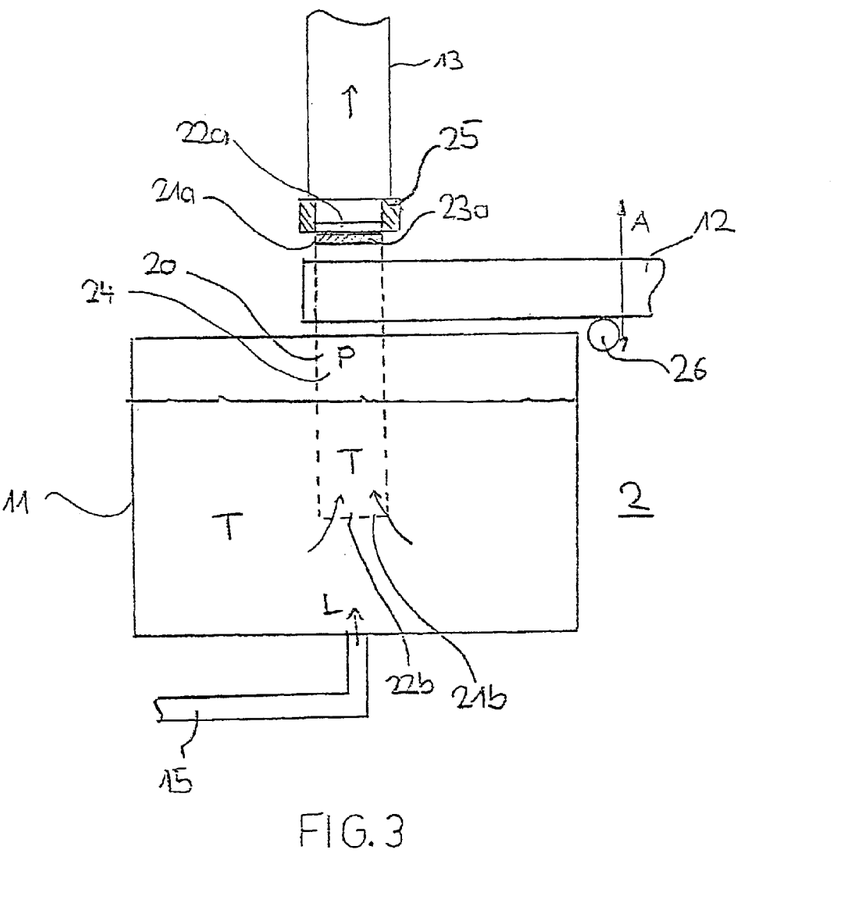
FIG. 3 is a schematic of the filling process as claimed in the invention.

FIG. 3 shows (enlarged) the column 20 in the fill station 2. The column 20 is connected on its top end 21a by the coupling piece 25 to the connecting line 13. In the area of the top end 21a a first frit 23a is inserted in the intake opening 22a. A negative pressure P can be produced by means of the negative pressure source 24 in the interior 24 of the column 20 through the connecting line 13. In this way the separating medium T is taken into the interior 24 of the column 20 through the fill opening 22b on the bottom end 21b of the column 20. The interior 24 of the column is filled homogeneously in this way with the separating medium T as far as the frit 23a.

The separating medium T is fluidized by blowing air L through the pressure line 15 into the tank 11.

The separation column 20 is attached to the holding device 12. The attachment is not detailed. Attachment can take place for example by a clamp in a manner known to one skilled in the art.

The holding device is vertically adjustable in the axial direction A. A stop 26 limits the axial motion downward and thus defines the maximum immersion depth of the column 20 in the container 11.

Figure 4A:
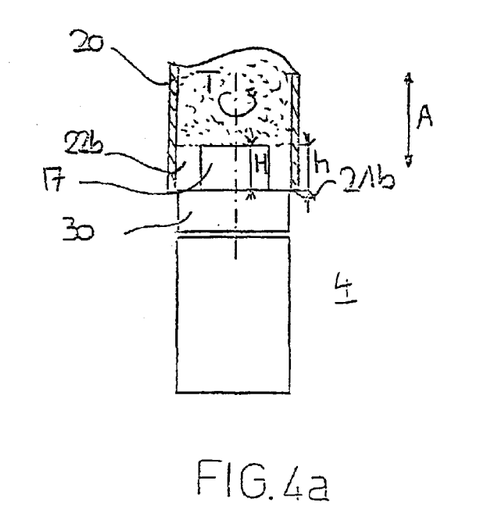
FIGS. 4, 4b are a schematic of the cleaning process or a cleaning station as claimed in the invention.
Figure 4B:
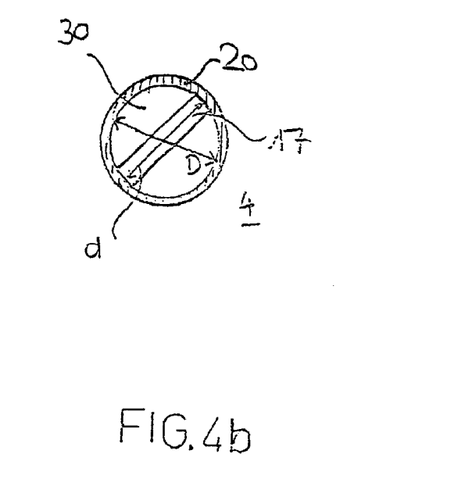

FIGS. 4a and 4b show a schematic of the cleaning station 4 in a side view FIG. 4a) and in a top view (FIG. 4b).

The cleaning station has a mounting 30 on which there is a rotary doctor blade 17. The doctor blade 17 has radially outer sides which extend along the free inside surface of the separation column. To remove the excess separating material T in the area of the fill opening 22b on the bottom end 21b of the separation column 20, the column is lowered in the axial direction A with the holding device 12 until the bottom end 21b rests roughly on the mounting 30. The doctor blade 17 penetrates into the opening 22b on the bottom end 21b of the column 20. The height H of the doctor blade corresponds roughly to the length h of the section in which the separating material T is to be removed. FIG. 4b shows an overhead view of the doctor blade 17. The outside diameter d of the doctor blade 17 corresponds substantially to the free inside diameter D of the column 20. By turning the doctor blade 17 the excess material is removed on the bottom end 21b. At the same time a perfectly straight horizontal termination surface of the separating material T is produced.

As soon as the excess separating material T has been removed, the separation column 20 is again lifted in the axial direction A. Because the separation column 20 is still connected to the negative pressure source 14, the separating material T is also held in the separation column 20 against the force of gravity.

Figure 5:
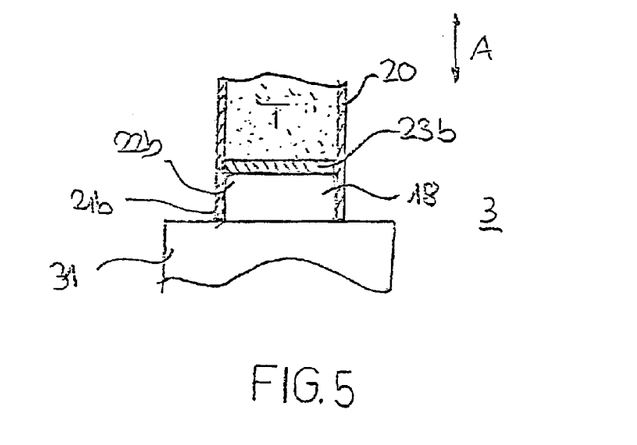
FIG. 5 is a schematic of the sealing station as claimed in the invention.

FIG. 5 schematically shows the sealing station 3, The sealing station 3 has a storage area 18. A second frit 23b is deposited on the storage area 18. By lowering the separation column 20 onto the sealing station 3 the frit 23b can be inserted into the opening 22b on the bottom end 21b of the column 20. The column 20 is lowered until its bottom end 21b rests on a mounting 31 for the storage area 18. The dimension of the frit 23b is chosen such that it remains stationary within the column 20 as a result of sliding friction. By lifting the column 20 in the axial direction A the column is removed from the sealing station 3. The column 20 is homogeneously filled with the separating medium T and is closed on both sides with the frit 23a, 23b. To end the filling process, the connecting line 13 is interrupted with a valve arrangement 19 (see FIG. 6) so that normal pressure can be reestablished through the fill opening 22b in the interior 24 of the column 20. As soon as normal pressure has been established, for example after waiting a few seconds, the coupling piece 25 can be removed from top end 21a of the column 20 and the column can be removed from the holding device.

Figure 6:
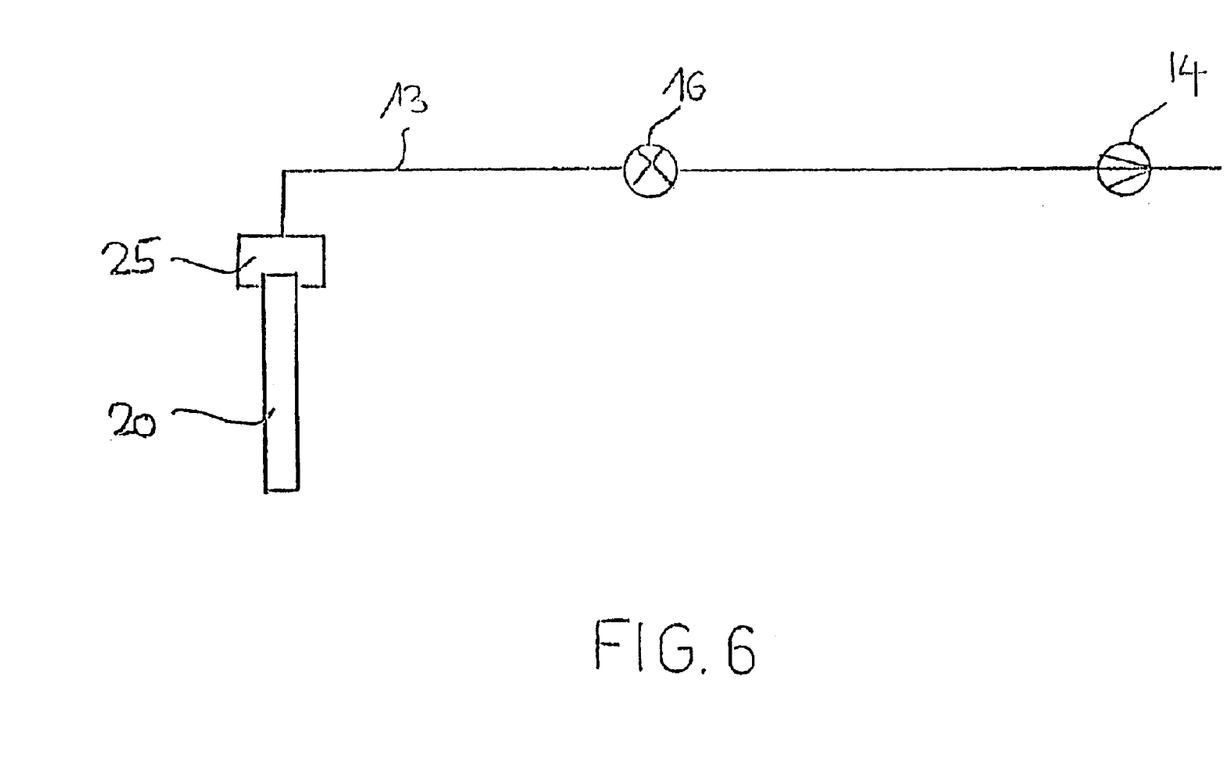
FIG. 6 is a schematic of the connection between the column and the negative pressure source as claimed in the invention and FIG. 7 shows an enlargement of the coupling piece.

FIG. 6 schematically shows the connection between the column 20 and the negative pressure source 14 by means of the coupling piece 25, the connecting line 13 and a valve 16 which has been inserted into the connecting line 13.

Figure 7:
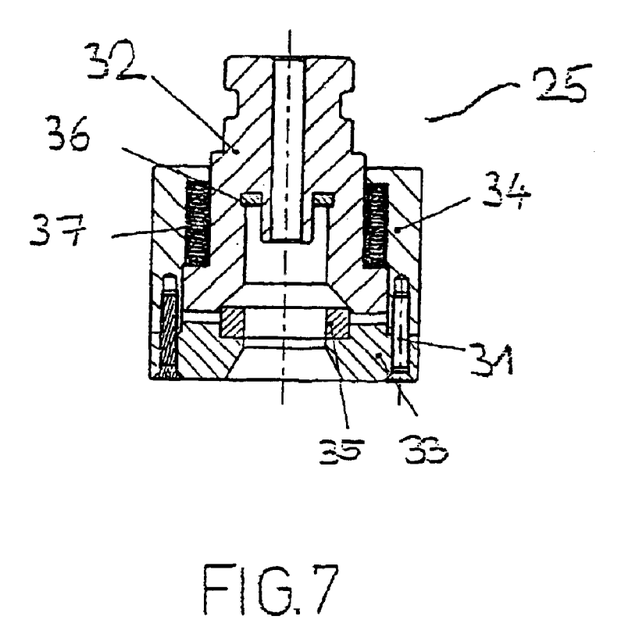

FIG. 7 shows an enlargement of the coupling piece 25 for use in this invention. The coupling piece includes a clamp sleeve 32 for connection to the connecting line 13. In the clamp sleeve 32 a flat seal 36 is inserted against which the top end 21a of the column 20 can be pressed. A clamping ring 35 is clamped between the clamp sleeve 32 and the cover 33. The cover 33 is connected via screws 31 to a handling sleeve 34 which is pretensioned on the clamp sleeve 32 by means of a compression spring 37. The column 20, as is used in the coupling piece 25, tightly adjoins the flat seal 36 and is held by the clamping ring 35.

Since the invention is subject to modifications and variations, it is intended that the foregoing description and the accompanying drawings shall be interpreted as only illustrative of the invention defined by the following claims.

I claim:

1. A device for filling a column which is open on two ends with a filler material, said device comprising
   a tank for holding the filler material,
   a holding device for holding the column, and
   a connecting line for airtight connection of the intake opening on one end of the column to a negative pressure source, wherein the holding device comprises means for inserting the column into the tank at least with one fill opening arranged on an other end of the column and wherein a negative pressure can be produced with the negative pressure source to suck the filler material out of the tank into the column, and wherein the tank has means for fluidizing the filler material.

2. A device as claimed in claim 1, wherein the fluidizing means are formed by a compressed air source by means of which a gas can be blown into the tank.

3. A device as claimed in claim 1, wherein the column can be moved by means of a holding device between a fill station, a sealing station and a cleaning station.

4. A device as claimed in claim 3, wherein the column can be swivelled along a circular path between the fill station, the cleaning station and the sealing station.

5. A device as claimed in claim 3, wherein the cleaning station has means for removing excess filler material in the area of the fill opening.

6. A device as claimed in claim 5, wherein the removal means comprises a rotary doctor blade.

7. A device as claimed in claim 3, wherein the sealing station typically has means for inserting a sealing body into the fill opening on the end of the column.

8. A device as claimed in claim 1, wherein the holding device is vertically adjustable so that the column can be immersed in the filler material in the tank by lowering the holding device along one axis.

9. A device as claimed in claim 1, wherein the negative pressure source is designed to produce a negative pressure from 1 mbar to 400 mbar.

10. A device as claimed in claim 1, wherein the connecting line has a valve arrangement for closing the connecting line.

11. A device as claimed in claim 1, wherein the holding device has a stop for limiting the immersion depth of the column in the filler material.

12. A process for filling a column which is open on two ends with a filler material, said method comprising steps of inserting the column at least with one fill opening into a tank containing filler material, producing a negative pressure in the interior of the column or sucking the filler material through a fill opening on one end of the column into the column, and removing the filled column from the tank and sealing said fill opening, wherein the filler material is fluidized in the tank before or during filling of the column.

13. A process as claimed in claim 12, wherein the column is lowered with the fill opening on its bottom end into the tank.

14. A process as claimed in claim 12, wherein the column is cleaned before sealing at least in the area of the fill opening, and excess separating material present in the area of the fill opening is removed.

15. A process as claimed in claim 12, wherein before filling the column the column is sealed in the intake opening on the other end of the column with an air-permeable sealing element.

16. A process as claimed in claim 12, wherein the filler material is fluidized in the tank before or during filling of the column by blowing a gas into the tank.

* * * * *